United States Patent [19]

Young

[11] Patent Number: 5,173,742
[45] Date of Patent: Dec. 22, 1992

[54] DOUBLE BEAM DETECTOR SYSTEM FOR LIQUID CHROMATOGRAPHY

[75] Inventor: Eugene F. Young, Wilton, Conn.

[73] Assignee: The Perkin-Elmer Corporation, Norwalk, Conn.

[21] Appl. No.: 751,415

[22] Filed: Aug. 28, 1991

[51] Int. Cl.$^5$ .......................... G01J 3/42; G01N 21/31
[52] U.S. Cl. ................................ 356/319; 250/373; 356/435; 356/440
[58] Field of Search ............... 356/319, 326, 328, 246, 356/435, 436, 410, 411, 440; 250/373

[56] References Cited

U.S. PATENT DOCUMENTS

| | | | |
|---|---|---|---|
| 3,516,752 | 6/1970 | Hrdina | 356/246 |
| 3,591,801 | 7/1971 | Watson | 356/435 |
| 3,614,242 | 10/1971 | Hrdina | 356/410 |
| 3,792,929 | 2/1974 | Alpert . | |
| 3,795,450 | 3/1974 | Munk | 356/246 |
| 4,011,451 | 3/1977 | Nelson | 356/246 |
| 4,037,974 | 7/1977 | Fletcher et al. | 356/246 |
| 4,094,609 | 6/1978 | Fujii et al. | 356/435 |
| 4,886,356 | 12/1989 | Paradis | 356/246 |

FOREIGN PATENT DOCUMENTS

| | | | |
|---|---|---|---|
| 128328 | 7/1985 | Japan | 356/246 |
| 105445 | 5/1986 | Japan | 356/246 |
| 225636 | 10/1986 | Japan | 356/246 |
| 2116707 | 3/1982 | United Kingdom . | |

OTHER PUBLICATIONS

Mathematics of Statistics, Kenney & Keeping, Van Nostrand Co. Inc., Princeton, N.J. (2nd ed 1959, pp. 59–60).

*Primary Examiner*—F. L. Evans
*Attorney, Agent, or Firm*—H. S. Ingham; E. T. Grimes

[57] ABSTRACT

A double beam detector system for liquid chromatography includes a light source and slits to effect two beams of radiation symmetrical to an optical axis and focused through a common point. A concave reflective dispersion grating is disposed on the optical axis which is folded at the grating. A collimating lens directs the beams parallel to the optical axis into a pair of detector cells. The collimating lens and entrance lenses for the cells are selected so that the common point is imaged on exit windows of the cells. The grating has a curvature selected cooperatively with the collimating lens, entrance lenses and relevant distances so as to focus the entrance slits at respective entrance windows for the cells. The beam size is constricted to less than the cell bore size by selected parameters of the collimating lens and the entrance lenses.

10 Claims, 2 Drawing Sheets

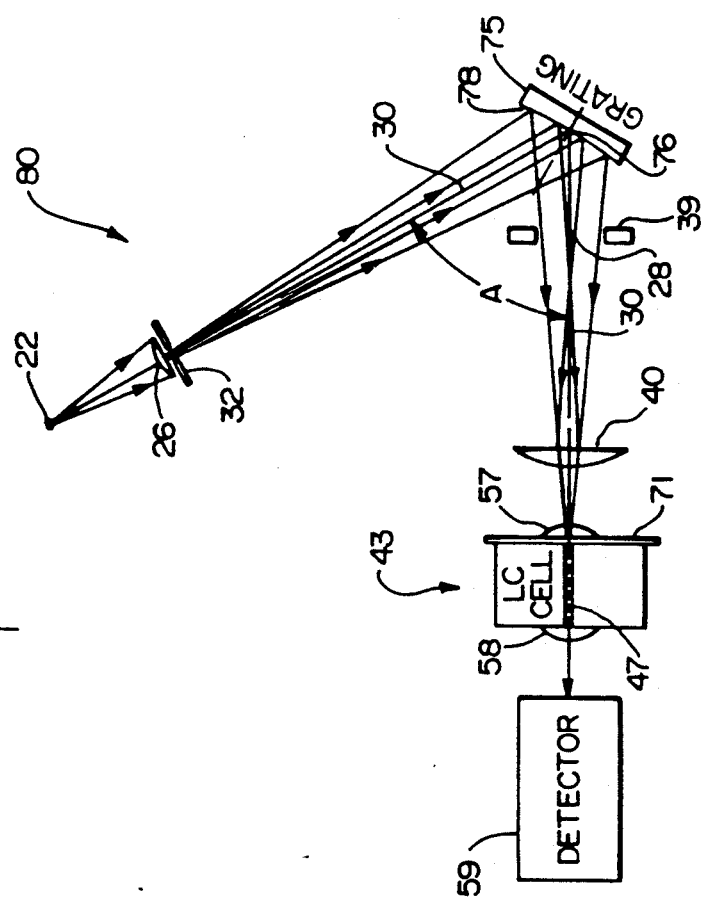
FIG. 3
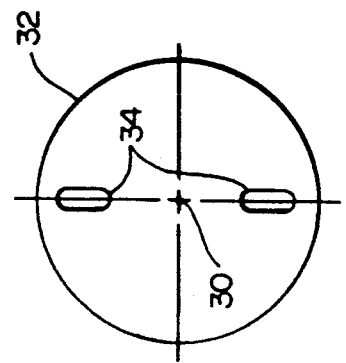
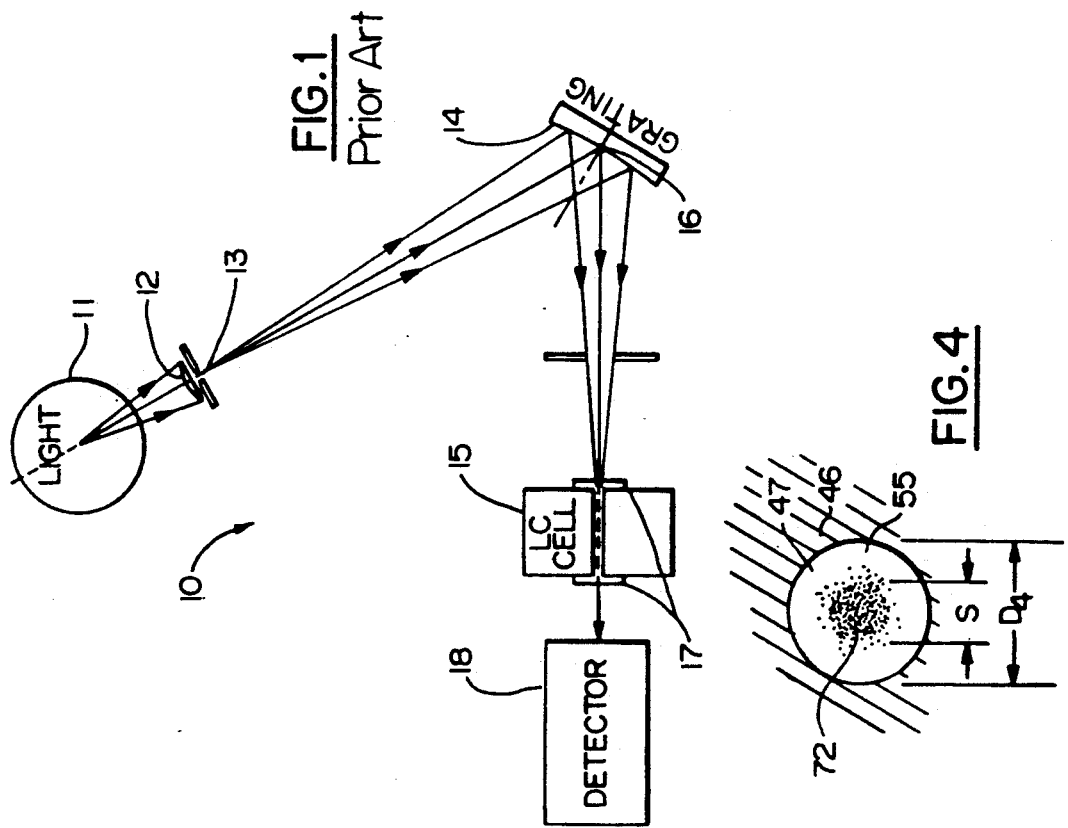
FIG. 5
FIG. 1 Prior Art
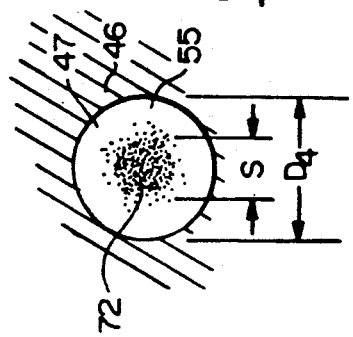
FIG. 4

DOUBLE BEAM DETECTOR SYSTEM FOR LIQUID CHROMATOGRAPHY

The present invention relates to liquid chromatography and particularly to a double beam detector system for liquid chromatography.

BACKGROUND OF THE INVENTION

In spectrophotometers for liquid chromatography (LC) a substance whose quantitative presence in a sample is to be determined is injected and dissolved into a suitable liquid carrier solvent, separated in an LC column and flowed through a detector cell which has end windows through which a selected wavelength of ultraviolet or visible light radiation is directed. Radiation exiting from the cell falls on a photodetector having an output recorded by suitable instrumentation which is calibrated to indicate the amount of radiation absorbed by the fluid flowing through the cell. Absorbance is customarily indicated by a graph continuously recorded on a strip chart by a pen recorder. The quantitative presence of a sample substance of interest is determined by measuring the area under the graph peaks which represent the amount of radiation of a particular wavelength that is absorbed, particular materials being identified by particular wavelengths characteristically absorbed by them.

The sensitivity of a spectrophotometer detector cell is a function particularly of the stability of the base line of the graph. The graph base line is established by the absorbance of the solvent used, and will change in relation to any change in the refractive index of the solvent. The refractive index in turn will be changed by a change in the temperature of the solvent in the cell, or by a transient as a test sample reaches the cell. Transients are particularly associated with temporary changes in refractive index on the fluid near the wall of the cell. When the baseline changes, the true peak area cannot be measured accurately and the peaks themselves become less clearly defined and hence difficult to identify and measure with any reliable degree of accuracy. The sensitivity of the instrument is disproportionally reduced by any change in temperatures or composition of the solvent, thus altering its index of refraction and increasing flow noise.

FIG. 1 shows a prior art type of LC detector system 10. A light source 11 provides light to a field lens 12 adjacent to a slit 13 oriented perpendicular to the plane of the drawing. A concave grating 14 is disposed to receive light from the slit and focus the same into a pair of flow cells; one such cell 15 is shown in the drawing, the other being above or below the plane of the drawing. Orientation of the grating about a vertical axis 16 at the central reflection point determines a wavelength incident on both of the cells. End windows 17 retain flowing liquid in the cell bores. A photodetector 18 after each cell detects the amount of light transmitted. One cell is used as a standard for comparison of the other receiving sample injected into the liquid.

U.S. Pat. No. 4,886,356 of the present assignee discloses a detector cell assembly useful for liquid chromatography. A problem suggested in the patent is effect of transients due to temperature changes causing nonuniform index of refraction of the liquid in the cell. Thermal insulation offered by the patent disclosure, or in other cases a heat sink, alleviate the temperature effects; however similar effects may result when test sample injected into the liquid reaches the cell, before equilibrium is reached. Small size of such cells is directed to minimizing such effects but has become insufficient for improved sensitivity and accuracy.

U.S. Pat. No. 4,011,451 discloses a lens for directing beams of light onto a pair of cells which are diverging so as to keep aberrant light from the walls. U.S. Pat. No. 4,037,974 discloses various methods for blocking light reflected from or through the cell walls. U.S. Pat. No. 3,792,929 discloses a field lens for tunneling radiation through the cell without striking the walls. U.K. Patent Application GB 2 116 707 A is directed to minimizing boundary effects in the cell with the use of a field stop and an aperature stop in the optical train directing light into the cell.

SUMMARY OF THE INVENTION

An object of the invention is to provide a double t,eam detector system for liquid chromatography, which is relatively low in cost, is low in detector noise and drift, and has reduced sensitivity to spurious effects from sample injections and temperature fluctuations.

The foregoing and other objects are achieved by a double beam detector system for liquid chromatography, including a source of radiation, slit means disposed relative to the source of radiation to effect two beams of radiation symmetrical to an optical axis, and collimating means disposed to direct the two beams along respective beam axes parallel to the optical axis. A pair of parallel detector cells each includes a body having a cell bore therethrough with open ends, with each cell bore having a bore diameter and a bore axis coinciding with a beam axis such that one of the beams passes through each cell bore. The detector cells further have transparent entrance and exit windows respectively closing the ends of the bores, and means for flowing liquid through each cell bore. A pair of radiation detectors are each aligned with a cell bore so as to be receptive of a beam passed therethrough.

Constriction means constrict each beam to a beam size in a respective cell bore, the beam size being less than the bore diameter. Preferably the constricting means comprises the collimating lens and the entrance lenses forming a pair of optical trains each having optical parameters selected cooperatively so that the common point is imaged with a spot size, the spot size being such that the sum of the image of the radiation source (generally stopped) and the spot size is less than each bore diameter.

In preferred embodiments the system further comprises a pair of entrance lenses each forming an entrance window, and a field lens disposed adjacently to the slit means so as to focus the two beams through a common point on the optical axis between the slit means and the entrance lenses. The collimating means comprises a collimating lens centered on the optical axis between the common point and the entrance lenses. The collimating lens and each of the entrance lenses are selected cooperatively so that the common point is imaged on each of the exit windows.

In a further embodiment the system comprises a concave reflective dispersion grating positioned on the optical axis between the slit means and the collimating lens. The optical axis is folded at the grating at an angle selected to provide a selected order of dispersion in the beams at the detector cells. The slit means is symmetrical to a diametric line passing perpendicularly through the optical axis, and the grating is oriented so that the dispersion is perpendicular to the diametric line with the beams comprising a selected wavelength, band of radiation in the cell bores. The grating has a curvature selected cooperatively with the collimating lens, entrance lenses and relevant distances so as to focus the entrance slits at respective entrance windows.

BRIEF DESCRIPTION OF THE DRAWINGS

FIG. 1 is a schematic diagram of a prior art double beam detector system for liquid chromatography.

FIG. 3 is an end view of a mask component of FIG. 2.

FIG. 4 is a sectional view taken at 4—4 of FIG. 2.

FIG. 5 is a schematic diagram of a system according to a further embodiment of the present invention.

DETAILED DESCRIPTION OF THE INVENTION

Figure 2:
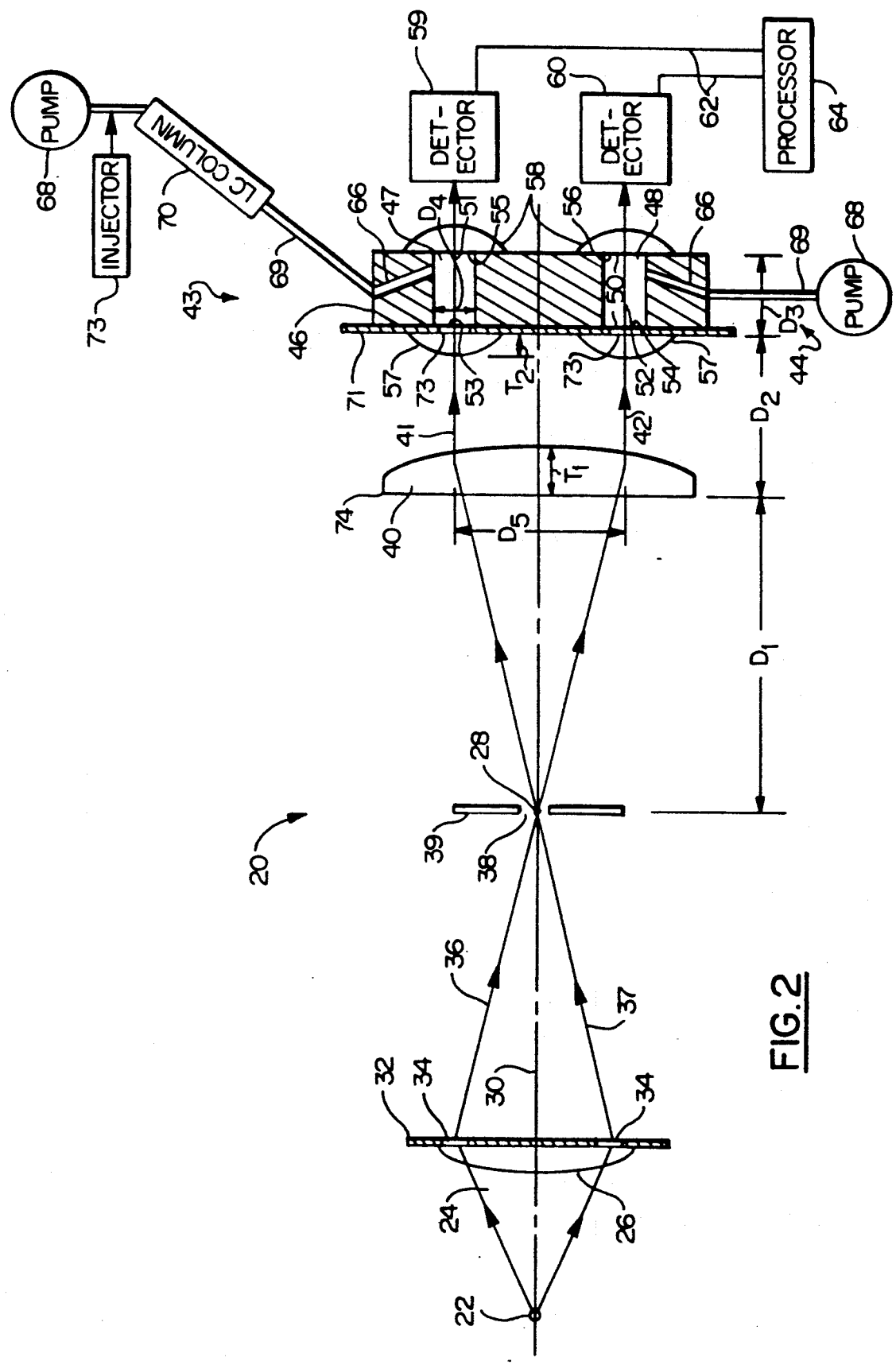
FIG. 2 is a schematic diagram of a double beam detector system according to the present invention.

FIG. 2 shows a simpler aspect of the invention for a double beam detector system 20 for liquid chromatography. A small radiation source 22 such as a deuterium lamp provides light radiation 24 to a field lens 26 which focusses the source to a point 28 on the optical axis 30. A slit means 32 adjacent to the field lens consists of an opaque disk with two slits 34 therein spaced diametrically from the axis as shown in FIG. 3. The slits are thus disposed relative to the light source so as to define two beams 36, 37 of radiation symmetrical to the optical axis, the beams passing through the common object point 28 coinciding with the focus point. A stop 39 with a field aperature 38 may be placed at this point. A collimating lens 40 is centered on the axis to be receptive of the beams after the common object point and direct the two beams along respective beam axes 41, 42 parallel to each other.

The two entrance slits 34 may be replaced by a single long slit (not shown), as the central portion of the radiation passing through such a slit will be blocked further along the optical train. Thus only the outer portions of the radiation are of consequence. However the use of two slits is preferred so as to reduce stray radiation. The terms "two beams" or "the beams" are used herein and in the claims to mean either separate beams from the separate slits, or the outer portions of the radiation from a single long slit.

A pair of parallel liquid chromatography (LC) detector cells 43, 44 are formed, conveniently in a single body 46 although separate bodies may be used. Each cell is generally of the conventional type, for example as described in the aforementioned U.S. Pat. No. 4,886,356. Each cell has a cell bore 47, 48 through the body with open ends 50. Each bore has a bore axis 51, 52 coinciding with a beam axis 41, 42 such that one of the beams passes through each cell bore. The detector cells further have transparent entrance windows 53, 54 and exit windows 55, 56 respectively closing the ends of the bores. Preferably the windows are the planar inner surfaces of respective plano convex lenses 57, 58 as described below. A pair of conventional photodetectors 59, 60 are each aligned with a cell bore so as to be receptive of a beam passed therethrough and out of the exit windows. Each exit window/lens focuses its beam into a detector. Output signals from the detectors are conveyed on lines 62 to a processing system 64 for comparative analysis and presentation of results.

Means for flowing liquid through each cell bore include passages 66 leading to each end of the bore (one passage shown for each bore). The inlet passages are receptive of liquid from a pump 68, through tubes 69, via an LC column 70 for at least one cell. Typically the flowing liquid for one cell will have a test sample from an injector 73 for analysis, and the other cell is used for comparison.

The size of the light source 22 and/or the size of the aperture 38 are sufficiently small so that the beams in the bores 47, 48 have a diameter, without regard to aberrations in the optics, substantially smaller than the diameters of the bores. Further means are provided to constrict each beam in the bores to a beam diameter less than the bore diameter. In one aspect this comprises a mask 71, similar to the mask 32 of FIG. 3, with two constricted openings 73 disposed adjacent to respective entrance windows.

The beam is constricted so as avoid transient effects in the index of refraction or optical absorption near the walls of the cell bores as test samples from an LC column in the liquid reach the cells, or in the event of temperature changes, before equilibrium is reached. Although the beam may be constricted by the openings, preferably the constriction is effected with the optics as explained below.

The collimating lens 40 and the entrance lenses 57 form a pair of parallel optical trains each having optical parameters selected cooperatively so that the common object point 28 is imaged on each exit window 55, 56. Advantageously the collimating lens consists of a hemispherical lens with a planar surface 74 facing away from the entrance lenses, and the entrance lenses each consists of a hemispherical lens with a planar surface functioning as a respective entrance window 53, 54. The selected optical parameters comprise indexes of refraction of all relevant lenses and liquid, radii of curvature and thicknesses $T_1$ and $T_2$ of the collimating lens and the entrance lenses, distance $D_1$ between the common point 28 and the planar surface 74 of the collimating lens, distance $D_2$ between the collimating lens and each entrance window, distance $D_3$ between the entrance window and the exit window (bore length), bore diameters $D_4$ and separation $D_5$ between bore axes.

To constrict the beam in the bore, the optics and field aperature are to provide for the image 72 (FIG. 4) having a size S less than the bore diameter $D_4$. The light source 22 is imaged onto the exit windows by way of an intermediate image at point 28. The theoretical image size (without aberrations) of the light source on the exit windows is the theoretical image size of the field aperture, or the image size of the source itself if sufficiently small. The defined image size S is the sum of the theoretical image size on the exit windows 55, 56 of the light source (generally as limited by aperature 38) and a spot size, the latter being an enlargement of the image due to aberrations. Conveniently the spot size is computed as twice a root-mean-square (rms) spot size, defined conventionally, for example as described in Mathematics of Statistics, Kenney & Keeping, Van Nostrand Co. Inc., Princeton, N.J. (2nd ed. 1959, pages 59–60). The spot size is computed from the assumption of a hypothetical point source located at the common object point 28. The finite spot size derives from the aberrations of imperfect optics, for example, the hemispherical shapes of the lenses. The spot size may be computed using conventional computer programming, for example with "Beam 3" program sold by Stellar Software, Berkeley, Calif.

Such a program generates ray paths through the optical components, for various ray angles initiating at the common object point 28 limited by the entrance aperture 73 and the exit bore diameters $D_4$. Ray angles are taken at equal increments, for example 0.2° increments from zero to 2° from the axis 30. An rms spot size is computed for a set of rays, with selected values for the aforementioned optical parameters. The process is repeated for various values until a minimum image size smaller than bore diameter is ascertained, preferably a minimized spot size. The image 72 in FIG. 4 is depicted as a radially decreasing density of points representing rays incident on the window 55. Generally certain of the parameters are predetermined or constrained by other factors, such as the indexes of refraction, distances between components, and bore dimensions and separation. Lens thicknesses may also be fixed. Thus iterations are made primarily with radii of the lens surfaces, and charges in other parameters such as distances are made if suitable results are not obtained with the initial selections. The ray computations also are used to determine appropriate dimensions for the collimating lens so as to yield the parallel beam axes coinciding with the bore axes.

In a preferred aspect of the invention, a detector system 80 further includes a concave reflective dispersion grating 75 as shown in FIG. 5. The conventional purpose of the grating is to provide for selections of narrow wavelength bands for liquid chromatographic analyses. However the choice of the concave grating and its specific placement in the system according to the invention provides for further preferable focusing. Other components in the system of FIG. 5 are the same as for FIG. 2, and are numbered accordingly. Further components such as windows are present but not shown for clarity. The foregoing descriptions for all of these components are incorporated by reference for FIG. 5, without repeating here.

The grating is disposed on the optical axis 30 between the slits 32 and the collimating lens 40. The optical axis is folded at the grating at an angle which provides a selected order of dispersion in the beams at the detector cells. For example with a 1200 lines/mm grating for zero order dispersion the axis is folded at an angle A of 61.6°. The grating may be rotatable about another axis 76 through the folding point perpendicular to the plane of the folded optical axis, so as to be oriented to select a wavelength band falling on the detector cells 59, 60.

The slits (also FIG. 3) are spaced symmetrically on a diametric line passing perpendicularly through the optical axis such that the beam axes are also diametrically spaced from the optical axis. The grating is oriented so that the dispersion is perpendicular to the diametric line, with the beams comprising a selected wavelength band of radiation in the cell bores. The grating has a curvature 78 selected cooperatively with the dimensions of the collimating and entrance lenses and their refractive indexes, and with distances between the entrance slit and the grating, the grating and the collimating lens, and the collimating lens and the entrance windows, so as to focus the entrance slits at respective entrance windows.

The mask 71 at the entrance windows in this case may additionally or alternatively serve to narrow the width of the wavelength band. Other configurations in the system with the grating are as described for FIG. 2, including the focusing of the common object point 28 on the exit window and the parameter selection to minimize rms spot size.

Selected parameters and computed dimensions are set forth in Table 1 to provide a specific example for a detector system according to the present invention.

TABLE 1

Source to slits: 44.4 mm
Slits to grating: 100 mm
Grating to collimating lens:* 74 mm
Collimating lens to entrance window ($D_2$): 20 mm
Length of cell bores ($D_3$): 10 mm
Diameter of cell bores ($D_4$): 1.0 mm
Spacing of beams at slits: 6.3 mm
Separation of bore axes ($D_5$): 4.1 mm
Focal length of field lens: 39.3 mm @ 0.3404 microns
Common point to collimating lens ($D_1$): 34.8 mm
Radius of grating: 112 mm
Radius of collimating lens: 17.76 mm
Thickness of collimating lens ($T_1$): 3.23 mm
Radius of entrance lens: 4.68 mm
Thickness of entrance lenses ($T_2$): 7: 2.87 mm
Refractive index of lenses: 1.47858 @ 0.3404 microns
Refractive index of liquid: 1.3333
Spot size (rms): 0.01 mm
Diameter of aperture 38: 2 mm
Diameter of image of aperture at exit window: 0.5 mm
Image size S: 0.52 mm
*Planar surface The double beam detector system of the present invention, particularly with the grating, is compact and relatively low cost with high performance. Transient effects of the refractive index of the liquid, temperature changes, and detector noise and drift are substantially reduced. Accuracy, stability and sensitivity are improved.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

I claim:

1. A double beam detector system for liquid chromatography, comprising:

a source of radiation;

slit means disposed relative to the source of radiation to effect two beams of radiation symmetrical to an optical axis;

collimating means disposed to direct the two beams along respective beam axes parallel to the optical axis;

a pair of parallel detector cells each including a body having a cell bore therethrough with open ends, each cell bore having a bore diameter and a bore axis coinciding with a beam axis such that one of the beams passes through each cell bore, the detector cells further including transparent entrance and exit windows respectively closing the ends of the bores, and means for flowing liquid through each cell bore;

a pair of radiation detectors each aligned with a cell bore so as to be receptive of a beam passed therethrough; and constriction means for constricting each beam to a beam size in a respective cell bore, the beam size being less than the bore diameter.

2. The apparatus of claim 1 further comprising a pair of entrance lenses each being adjacent to a corresponding entrance window, and a field lens disposed adjacently to the slit means so as to focus the two beams through a common point on the optical axis between the slit means and the entrance lenses, the collimating means comprising a collimating lens centered on the optical axis between the common point and the entrance lenses.

3. The apparatus of claim 2 wherein the constriction means comprises masking means with two openings therein each disposed adjacently to a respective entrance window.

4. The apparatus of claim 2 wherein the collimating lens and each of the entrance lenses are selected cooperatively so that the common point is imaged on each of the exit windows.

5. The apparatus of claim 4 wherein each of the entrance lenses consists of a planoconvex lens with a planar surface functioning as a respective entrance window.

6. The apparatus of claim 4 wherein the source of radiation has an image size on the exit windows, and the constricting means comprises the collimating lens and the entrance lenses forming a pair of optical trains each having optical parameters selected cooperatively so that the common point is imaged with a spot size, the spot size being such that the sum of the image size and the spot size is less than each bore diameter.

7. The apparatus of claim 6 wherein the collimating lens consists of a hemispherical lens with a planar surface facing away from the entrance lenses, each of the entrance lenses consists of a hemispherical lens with a planar surface functioning as a respective entrance window, and the optical parameters comprise radii of curvature and thicknesses of the collimating lens and the entrance lenses, distance between the common point and the collimating lens, distance between the collimating lens and each entrance lens, distance between the entrance lens and the exit window, bore diameters and separation between bore axes.

8. The apparatus of claim 6 wherein the spot size is twice a root-mean-square spot size.

9. The apparatus of claim 4 further comprising a concave reflective dispersion grating positioned on the optical axis between the slit means and the collimating lens, the optical axis being folded at the grating at an angle selected to provide a selected order of dispersion in the beams at the detector cells, the slit means being symmetrical to a diametric line passing perpendicularly through the optical axis, the grating being oriented so that the dispersion is perpendicular to the diametric line with the beams comprising a selected wavelength band of radiation in the cell bores, and the grating having a curvature selected cooperatively with the collimating lens, entrance lens and distances between the slit means and the grating, the grating and the collimating lens, and the collimating lens and the entrance windows, so as to focus the slit means at respective entrance windows.

10. The apparatus of claim 9 further comprising masking means with two constricted openings therein each disposed adjacently to a respective entrance window to effect the beams in the cell bores as a narrow wavelength band of radiation.

* * * * *